(12) United States Patent
Wideman et al.

(10) Patent No.: US 6,277,926 B1
(45) Date of Patent: Aug. 21, 2001

(54) RUBBER COMPOUNDS CONTAINING AROMATIC KETONE POLYSULFIDES

(75) Inventors: Lawson Gibson Wideman, Tallmadge; Shingo Futamura, Wadsworth, both of OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 09/438,167

(22) Filed: Nov. 11, 1999

Related U.S. Application Data

(62) Division of application No. 09/032,732, filed on Feb. 27, 1998, now Pat. No. 6,075,096.

(51) Int. Cl.[7] .................................................. C08C 19/22

(52) U.S. Cl. ............................................................ 525/351

(58) Field of Search ............................................... 525/351

(56) References Cited

U.S. PATENT DOCUMENTS 3,869,435    3/1975   Trivette, Jr. .

*Primary Examiner*—Christopher Henderson
(74) *Attorney, Agent, or Firm*—Bruce J Hendricks

(57) ABSTRACT

The present invention relates to rubber compounds containing aromatic ketone polysulfides of the formula:

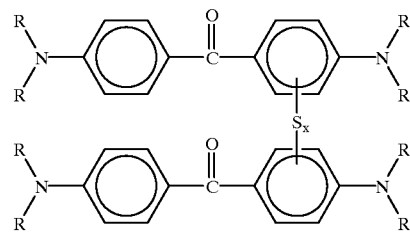

wherein R is selected from the group consisting of alkyls having from 1 to 18 carbon atoms and x is an integer of from 2 to 8.

4 Claims, No Drawings

RUBBER COMPOUNDS CONTAINING AROMATIC KETONE POLYSULFIDES

This is a Divisional of application Ser. No. 09/032,732, filed on Feb. 27, 1998, now U.S. Pat. No. 6,075,096.

BACKGROUND OF THE INVENTION

U.S. Pat. 4,894,409 discloses the use of 4,4'-bis-(dimethylamino)benzophenone as a polymer terminal molding agent.

U.S. Pat. 4,555,547 relates to a rubber composition containing a polybutadiene rubber that has a benzophenone compound bonded to a carbon atom of the polybutadiene molecular chain. An example of such a benzophenone compound is 4,4'-bis(alkyl-substituted amino) benzophenone.

U.S. Pat. 4,555,548 relates to a rubber composition containing a styrene-butadiene copolymer rubber and having bonded to a carbon atom of the rubber molecular chain a chemical moiety derived from a benzophenone compound. An example of such a benzophenone compound is 4,4'-bis (alkyl-substituted amino)benzophenone.

SUMMARY OF THE INVENTION

The present invention relates aromatic ketone polysulfides of the formula:

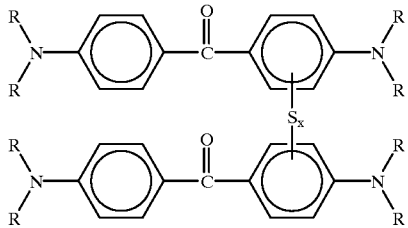

wherein R is selected from the group consisting of alkyls having from 1 to 18 carbon atoms and x is an integer of from 2 to 8.

DETAILED DESCRIPTION OF THE PREFERRED EMBODIMENT

The present invention also relates to a rubber composition containing from 0.1 to 10 phr of an aromatic ketone polysulfide of the formula:

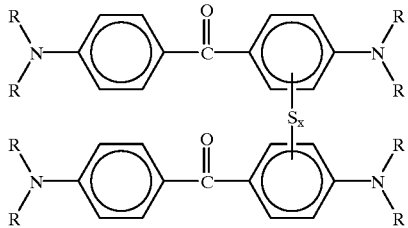

wherein R is selected from the group consisting of alkyls having from 1 to 18 carbon atoms and x is an integer of from 2 to 8. Preferably, R is an alkyl of from 1 to 2 carbon atoms and x is an integer of from 2 to 4.

In addition, there is disclosed a method for processing rubber comprising mixing with a rubber from 0.1 to 10 phr of an aromatic ketone polysulfide of the formula

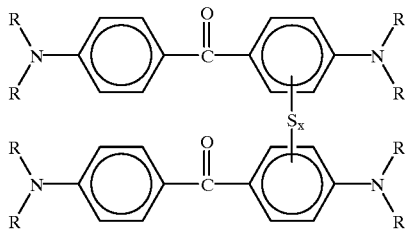

wherein R is selected from the group consisting of alkyls having from 1 to 18 carbon atoms and x is an integer of from 2 to 8.

The polysulfides used in the present invention may be present at various levels in the rubber compounds of the present invention. For example, the level may range from about 0.1 to 10.0 parts by weight per 100 parts by weight of rubber (also known as "phr"). Preferably, the level ranges from about 0.5 to about 5.0 phr.

The polysulfides may be prepared by reacting a suitable bis(alkylamino)benzophenone with a sulfur compound. Representative of suitable bis(alkylamino)benzophenone compounds which may be used include the 3,3', 3,4 and 4,4' isomers of
bis(dimethylamino)benzophenone,
bis(diethylamino)benzophenone,
bis(dipropylamino)benzophenone,
bis(dibutylamino)benzophenone,
bis(dipentylamino)benzophenone,
bis(dihexylamino)benzophenone,
bis(dihexylamino)benzophenone,
bis(dioctylamino)benzophenone,
bis (dinonylamino)benzophenone
bis(didecylamino)benzophenone,
bis(diundecylamino)benzophenone,
is (didodecylamino)benzophenone
bis(ditridecylamino)benzophenone,
bis(ditetradecylamino)benzophenone,
bis(dipentadecylamino)benzophenone,
is(dihexadecylamino)benzophenone,
bis(diheptadecylamino)benzophenone and
bis(dioctadecylamino)benzophenone.

Representative examples of sulfur compounds which may be used include sulfur monochloride and sulfur dichloride. Preferably, the sulfur compound is sulfur monochloride.

The bis(alkylamino)benzophenone is reacted with a sulfur compound under suitable conditions to form the polysulfide of the formula. The bis(alkylamino)benzophenone may be reacted with sulfur in a variety of mole ratios. Generally, the mole ratio of the bis(alkylamino)benzophenone to the sulfur ranges from about 1.0:0.5 to about 1.0:10.0 with a range of from about 1.0:6.0 to about 1.0:2.0 being preferred.

When the sulfur compound is halogenated, such as sulfur monochloride, it is preferred to conduct the reaction between the sulfur compound and the bis(alkylamino)benzophenone in the presence of a scavenger or "neutralizer" which does not interfere with the polysulfide formation. Representative examples include triethylamine, pyridines such as methyl pyridine and the like.

In accordance with Formula I, x is an integer of from 2 to 8. Preferably, x is an integer of from 2 to 4. When a higher mole ratio of the benzophenone compound to sulfur is used, the lower integers for x are realized. When a lower mole ratio of benzophenone compound to sulfur is used, the higher integers for x are realized.

The reaction conditions conducive to producing polysulfides where x is a lower integer are shorter reaction times and lower reaction temperatures. The reaction conditions conducive to producing polysulfides when x is a higher integer are longer reaction times and higher reaction temperatures.

An organic solvent may be used to dissolve the benzophenone compound. The solvent is preferably inert to the reaction between the bis(alkylamino)benzophenone and the sulfur compound. Illustrative of solvents suitable for use in the practice of this invention include: saturated and aromatic hydrocarbons, e.g., hexane, octane, dodecane, naphtha, decalin, tetrahydronaphthalene, kerosene, mineral oil, cyclohexane, cycloheptane, alkyl cycloalkane, benzene, toluene, xylene, alkyl-naphthalene, and the like; acetone; ethers such as tetrahydrofuran, tetrahydropyran, diethylether, 1,2-dimethoxybenzene, 1,2-diethoxybenzene, the dialkylethers of ethylene glycol, propylene glycol, butylene glycol, diethylene glycol, dipropylene glycol, oxyethyleneoxypropylene glycol, and the like; fluorinated hydrocarbons that are inert under the reaction conditions such as perfluoroethane, monofluorobenzene, and the like. Another class of solvents are sulfones such as dimethylsulfone, diethylsulfone, diphenolsulfone, sulfolane, and the like. Mixtures of the aforementioned solvents may be employed so long as they are compatible with each other under the conditions of the reaction and will adequately dissolve the bis(alkylamino)benzophenone compound and not interfere with the reaction.

The reaction between the bis(alkylamino)benzophenone and the sulfur compound to form the aromatic ketone polysulfides is exothermic and may be conducted over a wide temperature range. The temperature may range from moderate to an elevated temperature. In general, the reaction may be conducted at a temperature of between about 0° C. to 150° C. The preferred temperature range is from about 50° C. to 120° C., while the most preferred temperature range is from about 80° C. to 100° C.

The reaction pressure to form the aromatic ketone polysulfides is not deemed to be critical. Pressures ranging from about 0 kPa to 689 kPa may be used.

The reaction is preferably conducted in a nitrogen atmosphere.

The process for the preparation of the aromatic ketone polysulfides may be carried out in a batch, semi-continuous or continuous manner. The reaction may be conducted in a single reaction zone or in a plurality or reaction zones, in series or in parallel. The reaction may be conducted intermittently or continuously in an elongated tubular zone or in a series of such zones. The material of construction of the equipment should be such as to be inert during the reaction. The equipment should also be able to withstand the reaction temperatures and pressures. The reaction zone can be fitted with internal and/or external heat exchangers to control temperature fluctuations. Preferably, an agitation means is available to ensure the uniform reaction. Mixing induced by vibration, shaker, stirrer, rotating, oscillation, etc. are all illustrative of the types of agitation means which are contemplated for use in preparing the composition of the present invention. Such agitation means are available and well known to those skilled in the art.

Use of the aromatic ketone polysulfides improve the polymer-filler interaction of "elastomers or rubbers." The term "elastomer or rubber" as used herein embraces both vulcanized forms of natural and all its various raw and reclaim forms as well as various synthetic rubbers. The synthetic elastomers include conjugated diene homopolymers and copolymers and copolymers of at least one conjugated diene and aromatic vinyl compound. Representative synthetic polymers include the homopolymerization products of butadiene and its homologues and derivatives, as for example, methyl-butadiene, dimethylbutadiene and pentadiene as well as copolymers, such as those formed from butadiene or its homologues or derivatives with other unsaturated organic compounds. Among the latter are acetylenes, for example, vinyl acetylene; olefins, for example, isobutylene, which copolymerizes with isoprene to form butyl rubber; vinyl compounds, for example, acrylic acid, acrylonitrile (which polymerizes with butadiene to form NBR), methacrylic acid and styrene, the latter polymerizing with butadiene to form SBR, as well as vinyl esters and various unsaturated aldehydes, ketones and ethers, e.g. acrolein, methyl isopropenyl ketone and vinylethyl ether. Also included are the various synthetic rubbers prepared by the homopolymerization of isoprene and the copolymerization of isoprene and other diolefins in various unsaturated organic compounds. Also included are the synthetic rubbers such as 1,4-cis-polybutadiene and 1,4-cis-polyisoprene and similar synthetic rubbers.

Specific examples of synthetic rubbers include neoprene (polychloroprene), polybutadiene (including trans- and cis-1,4-polybutadiene), polyisoprene (including cis-1,4-polyisoprene), butyl rubber, copolymers of 1,3-butadiene or isoprene with monomers such as styrene, acrylonitrile and methyl methacrylate as well as ethylene/propylene terpolymers, also known as ethylene/propylene/diene monomer (EPDM) and, in particular, ethylene/propylene/ dicyclopentadiene terpolymers and styrene/isoprene/ butadiene rubber. The preferred synthetic rubbers for use in the present invention are polybutadiene, polyisobutylene, butadiene-styrene copolymers and cis,1,4-polyisoprene.

Vulcanization of the rubber compound of the present invention is generally carried out at conventional temperatures ranging from about 100° C. and 200° C. Preferably, the vulcanization is conducted at temperatures ranging from about 110° C. to 180° C. Any of the usual vulcanization processes may be used such as heating in a press or mold, heating with superheated steam or hot air or in a salt bath.

In addition to the aromatic ketone polysulfides, other rubber additives may also be incorporated in the rubber compound. The additives commonly used in rubber vulcanizates are, for example, carbon black, tackifier resins, processing aids, antioxidants, antiozonants, stearic acid, activators, waxes, phenol-formaldehyde resins, oils and peptizing agents. As known to those skilled in the art, depending on the intended use of the rubber compound, certain additives mentioned above are commonly used in conventional amounts. Typical additions of carbon black comprise about 20 to 100 parts by weight per 100 parts by weight of rubber (phr), preferably 30 to 80 phr. Typical amounts of tackifier resins comprise about 1 to 5 phr. Typical amounts of antioxidants comprise 1 to about 10 phr. Typical amounts of antiozonants comprise 1 to about 10 phr. Typical amounts of stearic acid comprise 1 to about 2 phr. Typical amounts of zinc oxide comprise 2 to 5 phr. Typical amounts of waxes comprise 1 to 5 phr. Typical amounts of phenol-formaldehyde resins comprise 1 to 8 phr. Typical amounts of oils comprise 5 to 40 phr. Typical amounts of peptizers comprise 0.1 to 1 phr. The presence and relative amounts of the above additives are not an aspect of the present invention.

The rubber composition may contain a silica filler. The silica filler may be added in amounts ranging from 10 to 250 phr. Preferably, the silica is present in an amount ranging from 15 to 80 phr.

The commonly employed particulate precipitated silica used in rubber compounding applications can be used as the silica in this invention. These precipitated silicas include, for example, those obtained by the acidification of a soluble silicate, e.g., sodium silicate.

Such silicas might be characterized, for example, by having a BET surface area, as measured using nitrogen gas, preferably in the range of about 40 to about 600, and more usually in a range of about 50 to about 300 square meters per gram. The BET method of measuring surface area is described in the *Journal of the American Chemical Society,* Volume 60, page 304 (1930).

The silica may also be typically characterized by having a dibutylphthalate (DBP) absorption value in a range of about 100 to about 400, and more usually about 150 to about 300.

The silica might be expected to have an average ultimate particle size, for example, in the range of 0.01 to 0.05 micron as determined by the electron microscope, although the silica particles may be even smaller, or possibly larger, in size.

Various commercially available silicas may be considered for use in this invention such as, only for example herein, and without limitation, silicas commercially available from PPG Industries under the HiSil trademark with designations 210, 243, etc; silicas available from Rhone-Poulenc, with, for example, designations of Z1165MP and Z165GR and silicas available from Degussa AG with, for example, designations VN2 and VN3, etc.

Whereas the sulfur containing bis-alkylaminobenzophenone improves the properties of a silica-filled rubber composition, the processing of the sulfur vulcanizable rubber may be conducted in the presence of a sulfur containing organosilicon compound. Examples of suitable sulfur containing organosilicon compounds are of the formula:

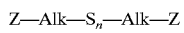 (II)

in which Z is selected from the group consisting of

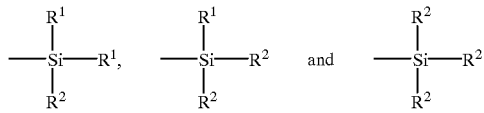

where $R^1$ is an alkyl group of 1 to 4 carbon atoms, cyclohexyl or phenyl;

$R^2$ is alkoxy of 1 to 8 carbon atoms, or cycloalkoxy of 5 to 8 carbon atoms;

Alk is a divalent hydrocarbon of 1 to 18 carbon atoms and n is an integer of 2 to 8.

Specific examples of sulfur containing organosilicon compounds which may be used in accordance with the present invention include: 3,3'-bis(trimethoxysilylpropyl) disulfide, 3,3'-bis(triethoxysilylpropyl)tetrasulfide, 3,3'-bis (triethoxysilylpropyl)octasulfide, 3,3'-bis(trimethoxysilyl-propyl)tetrasulfide, 2,2'-bis(triethoxysilylethyl)tetrasulfide, 3,3'-bis(trimethoxysilylpropyl)trisulfide, 3,3'-bis (triethoxysilylpropyl)trisulfide, 3,3'-bis(tributoxysilypropyl) disulfide, 3,3'-bis(trimethoxysilylpropyl)hexasulfide, 3,3'-bis(trimethoxysilylpropyl)octasulfide, 3,3'-bis(trioctoxy-silylpropyl)tetrasulfide, 3,3'-bis(trihexoxysilylpropyl) disulfide, 3,3'-bis(tri-2-ethylhexoxysilylpropyl)trisulfide, 3,3'-bis(triisooctoxysilylpropyl)tetrasulfide, 3,3'-bis(tri-t-butoxysilylpropyl)disulfide, 2,2'-bis(methoxy diethoxy silyl ethyl)tetrasulfide, 2,2'-bis(tripropoxysilylethyl) pentasulfide, 3,3'-bis(tricyclohexoxysilylpropyl)tetrasulfide, 3,3'-bis(tricyclopentoxysilylpropyl)trisulfide, 2,2'-bis(tri-2-methylcyclohexoxysilylethyl)tetrasulfide, bis(trimethoxy-silylmethyl)tetrasulfide, 3-methoxy ethoxy propoxysilyl 3'-diethoxybutoxysilylpropyltetrasulfide, 2,2'-bis(dimethyl-methoxysilylethyl)disulfide, 2,2'-bis(dimethylsec.-butoxysilylethyl)trisulfide, 3,3'-bis(methylbutylethoxy-silylpropyl)tetrasulfide, 3,3'-bis(di t-butylmethoxysilyl-propyl)tetrasulfide, 2,2'-bis(phenylmethyl methoxy-silylethyl)trisulfide, 3,3'-bis(diphenyl isopropoxysilyl-propyl)tetrasulfide, 3,3'-bis(diphenyl cyclohexoxysilyl-propyl)disulfide, 3,3'-bis(dimethyl ethylmercaptosilyl-propyl)tetrasulfide, 2,2'-bis(methyl dimethoxysilylethyl) trisulfide, 2,2'-bis(methyl ethoxypropoxysilylethyl) tetrasulfide, 3,3'-bis(diethyl methoxysilylpropyl)tetrasulfide, 3,3'-bis(ethyl di-sec.butoxysilylpropyl)disulfide, 3,3'-bis (propyldiethoxysilylpropyl)disulfide, 3,3'-bis(butyldi-methoxysilylpropyl)trisulfide, 3,3'-bis(phenyldimethoxy-silylpropyl)tetrasulfide, 3-phenylethoxybutoxysilyl 3'-trimethoxysilylpropyltetrasulfide, 4,4'-bis(trimethoxy-silylbutyl)tetrasulfide, 6,6'-bis(triethoxysilylhexyl) tetrasulfide, 12,12'-bis(triisopropoxysilyl dodecyl)disulfide, 18,18'-bis(trimethoxysilyloctadecyl)tetrasulfide, 18,18'-bis (tripropoxysilyloctadecenyl)tetrasulfide, 4,4'-bis (trimethoxysilyl-buten-2-yl)tetrasulfide, 4,4'-bis (trimethoxysilylcyclohexylene)tetrasulfide, 5,5'-bis (dimethoxymethylsilylpentyl)trisulfide, 3,3'-bis (trimethoxysilyl-2-methylpropyl)tetrasulfide, 3,3'-bis (dimethoxyphenylsilyl-2-methylpropyl)disulfide.

The preferred sulfur containing organosilicon compounds are the 3,3'-bis(trimethoxy or triethoxy silylpropyl) sulfides. The most preferred compound is 3,3'-bis (triethoxysilylpropyl)tetrasulfide. Therefore as to formula II, preferably Z is

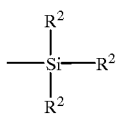

where $R^2$ is an alkoxy of 2 to 4 carbon atoms, with 2 carbon atoms being particularly preferred; Alk is a divalent hydrocarbon of 2 to 4 carbon atoms with 3 carbon atoms being particularly preferred; and n is an integer of from 2 to 5 with 4 being particularly preferred. The amount of the sulfur containing organosilicon compound of formula II in a rubber composition will vary depending on the level of silica that is used. Generally speaking, the amount of the compound of formula II, if used, will range from 0.01 to 1.0 parts by weight per part by weight of the silica. Preferably, the amount will range from 0.05 to 0.4 parts by weight per part by weight of the silica.

The vulcanization of the rubber compound is conducted in the presence of a sulfur-vulcanizing agent. Examples of suitable sulfur-vulcanizing agents include elemental sulfur (free sulfur) or sulfur donating vulcanizing agents, for example, an amine disulfide, polymeric polysulfide or sulfur olefin adducts. Preferably, the sulfur-vulcanizing agent is elemental sulfur. As known to those skilled in the art, sulfur-vulcanizing agents are used in an amount ranging from about 0.5 to 8 phr with a range of from 1.0 to 2.25 being preferred.

Accelerators are conventionally used to control the time and/or temperature required for vulcanization and to improve the properties of the vulcanizate. In some instances, a single accelerator system may be used, i.e., primary accelerator. Conventionally, a primary accelerator is used in amounts ranging from about 0.5 to 2.0 phr. In another instance, combinations of two or more accelerators may be used which may consist of a primary accelerator which is generally used in the large amount (0.5 to 2.0 phr), and a secondary accelerator which is generally used in smaller amounts (0.01–0.50 phr) in order to activate and to improve the properties of the vulcanizate. Combinations of these accelerators have been known to produce a synergistic effect of the final properties and are somewhat better than those produced by use of either accelerator alone. In addition, delayed action accelerators may be used which are not affected by normal processing temperatures but produce satisfactory cures at ordinary vulcanization temperatures. Suitable types of accelerators that may be used include amines, disulfides, guanidines, thiophthalimides, thioureas, thiazoles, thiurams, sulfenamides, dithiocarbamates and xanthates. Preferably, the primary accelerator is a sulfenamide. If a secondary accelerator is used, the secondary accelerator is preferably a guanidine, dithiocarbamate or thiuram compound.

The rubber compound may also contain a cure activator. A representative cure activator is methyl trialkyl ($C_8$–$C_{10}$) ammonium chloride, commercially available under the trademark Adogen from Sherex Chemical of Dublin, Ohio. The amount of activator may range from 0.05 phr to 5 phr.

The rubber compositions of the present invention may contain a methylene donor and a methylene acceptor. The term "methylene donor" is intended to mean a compound capable of reacting with a methylene acceptor (such as resorcinol or its equivalent containing a present hydroxyl group) and generate the resin in-situ. Examples of methylene donors which are suitable for use in the present invention include hexamethylenetetramine, hexaethoxymethylmelamine, hexamethoxymethylmelamine, lauryloxymethylpyridinium chloride, ethoxymethylpyridinium chloride, trioxan hexamethoxymethylmelamine, the hydroxy groups of which may be esterified or partly esterified, and polymers of formaldehyde such as paraformaldehyde. In addition, the methylene donors may be N-substituted oxymethylmelamines, of the general formula:

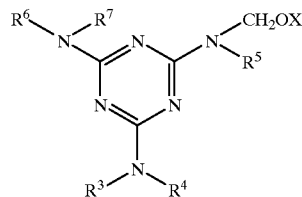

III wherein X is an alkyl having from 1 to 8 carbon atoms, $R^3$, $R^4$, $R^5$, $R^6$ and $R^7$ are individually selected from the group consisting of hydrogen, an alkyl having from 1 to 8 carbon atoms and the group —$CH_2OX$. Specific methylene donors include hexakis(methoxymethyl)melamine, N,N',N"-trimethyl/N,N',N"-trimethylolmelamine, hexamethylolmelamine, N,N',N"-dimethylolmelamine, N-methylolmelamine, N,N'-dimethylolmelamine, N,N',N"-tris(methoxymethyl)melamine and N,N'N"-tributyl-N,N', N"-trimethylol-melamine. The N-methylol derivatives of melamine are prepared by known methods.

The amount of methylene donor and methylene acceptor that is present in the rubber stock may vary. Typically, the amount of methylene donor and methylene acceptor that each is present will range from about 0.1 phr to 10.0 phr. Preferably, the amount of methylene donor and methylene acceptor that each is present ranges from about 2.0 phr to 5.0 phr.

The weight ratio of methylene donor to the methylene acceptor may vary. Generally speaking, the weight ratio will range from about 1:10 to about 10:1. Preferably, the weight ratio ranges from about 1:3 to 3:1.

The mixing of the rubber composition can be accomplished by methods known to those having skill in the rubber mixing art. For example the ingredients are typically mixed in at least two stages, namely at least one non-productive stage followed by a productive mix stage. The final curatives including sulfur vulcanizing agents are typically mixed in the final stage which is conventionally called the "productive" mix stage in which the mixing typically occurs at a temperature, or ultimate temperature, lower than the mix temperature(s) than the preceding non-productive mix stage (s). The rubber, silica, polysulfide of formula I and carbon black, if used, are mixed in one or more non-productive mix stages. The terms "non-productive" and "productive" mix stages are well known to those having skill in the rubber mixing art. The rubber composition containing the polysulfide of formula I vulcanizable rubber and generally at least part of the silica should, as well as the sulfur-containing organosilicon compound, if used, be subjected to a thermomechanical mixing step. The thermomechanical mixing step generally comprises a mechanical working in a mixer or extruder for a period of time suitable in order to produce a rubber temperature between 140° C. and 190° C. The appropriate duration of the thermomechanical working varies as a function of the operating conditions and the volume and nature of the components. For example, the thermomechanical working may be from 1 to 20 minutes.

Vulcanization of the rubber composition of the present invention is generally carried out at conventional temperatures ranging from about 100° C. to 200° C. Preferably, the vulcanization is conducted at temperatures ranging from about 110° C. to 180° C. Any of the usual vulcanization processes may be used such as heating in a press or mold, heating with superheated steam or hot air or in a salt bath.

The rubber compounds containing the aromatic ketone polysulfides may be used in the preparation of and, therefore, in the form of composite products including tires, power belts, conveyor belts, printing rolls, rubber shoe heels and soles, rubber wringers, automobile floor mats, mud flaps for trucks, ball mill liners, and the like. Preferably, the rubber vulcanizates are used in sidewall, tread, carcass ply, wirecoat or overlay compounds for tires.

The following examples are presented in order to illustrate but not limit the present invention.

Cure properties were determined using a Monsanto oscillating disc rheometer which was operated at a temperature of 150° C. and at a frequency of 11 hertz. A description of oscillating disc rheometers can be found in the Vanderbilt Rubber Handbook edited by Robert O. Ohm (Norwalk, Conn., R. T. Vanderbilt Company, Inc., 1990), pages 554–557. The use of this cure meter and standardized values read from the curve are specified in ASTM D-2084. A typical cure curve obtained on an oscillating disc rheometer is shown on page 555 of the 1990 edition of the Vanderbilt Rubber Handbook.

In such an oscillating disc rheometer, compounded rubber samples are subjected to an oscillating shearing action of constant amplitude. The torque of the oscillating disc embedded in the stock that is being tested that is required to oscillate the rotor at the vulcanization temperature is measured. The values obtained using this cure test are very significant since changes in the rubber or the compounding recipe are very readily detected.

The following tables report cure properties that were determined from cure curves that were obtained for the three rubber formulations that were prepared. These properties include torque maximum (Tmax), torque minimum (Tmin), delta torque (DEL T), minutes to 1 point of the torque increase (T1) and minutes to 90 percent of the torque increase (T90).

EXAMPLE 1

Preparation of 4,4'-Bis(dimethylamino) benzophenone Disulfide Compound

A 2-liter, round-bottom flask was charged with 53.7 g (0.2 mole) of 4,4'-bis(dimethylamino)benzophenone and 20.2 g (0.2 mole) of triethylamine in 250 ml of toluene. The solution was stirred under nitrogen as 13.5 g (0.1 mole) of sulfur monochloride was added dropwise. The reaction mixture exotherm increased the temperature to about 35° C. with an addition time of about 20 minutes. The reaction mixture was heated to 90–91° C. for an additional ½ hour with stirring. The mixture was treated with 250 ml of toluene with stirring and then with 500 ml of water, stirred and phase-separated. The organic layer was stripped of volatiles to give 57.9 g of a brown solid melting at 142–152° C. Small molecule GPC analysis shows sulfur weight pickup and the sulfur analysis (6.59 percent sulfur) gives x in Formula 1 as averaging one to two sulfurs.

EXAMPLE 2

Preparation of 4.4'-Bis(diethylamino)benzophenone Disulfide Compound

A reaction was carried out under the conditions of Example 1, except 50 g (0.15 mole) of 4,4'-bis (diethylamino)benzophenone and 15.6 g (0.15 mole) of triethylamine in 250 ml of toluene were charged into the reaction flask followed by 10.1 g (0.075 mole) of sulfur monochloride. Workup gave 45 g of a brown solid melting at 140–151° C. Small molecule GPC analysis shows sulfur weight pickup and the sulfur analysis (7.98 percent sulfur) gives x in Formula 1 as averaging one to two sulfurs.

EXAMPLE 3

Preparation of 4,4'-Bis(diethylamino)benzophenone Tetrasulfide Compound

A reaction was carried out under the conditions of Example 1, except 38.0 g (0.117 mole) of 4,4'-bis (diethylamino)benzophenone and 23.6 g (0.234 mole) of triethylamine in 250 ml of toluene were charged into the flask, followed by 15.6 g (0.117 mole) of sulfur monochloride. Workup gave 33 g of a brown solid melting at 143–1500C. Small molecule GPC analysis shows sulfur weight pickup and the sulfur analysis (14.8 percent sulfur) gives x in Formula 1 as averaging three to four sulfurs.

EXAMPLE 4

Physical Testing

Table I below shows the basic rubber compound that was used in this example. The rubber compound was prepared in a two-stage Banbury mix. All parts and percentages are by weight unless otherwise noted. All samples were prepared with the same procedure and ingredients except as to the use of the respective amount (phr) of ingredients listed in Table II. The cure data as well as other physical data for each sample are listed in Table II. In Table II, the various properties are reported for samples which were cured for 27 minutes at 150° C.

TABLE I

| Non-Productive | (phr) |
| --- | --- |
| Natural Rubber | 100.0 |
| Carbon Black (N121) | 49.0 |
| Polysulfide of Example 1, 2 or 3 | Varied |
| Zinc Oxide | 4.0 |
| Stearic Acid | 2.0 |
| Waxes | 1.5 |
| Antioxidants | 2.0 |
| Accelerator[1] | 0.20 |
| Accelerator[2] | 0.35 |
| Productive | (phr) |
| Sulfur | 1.0 |
| Accelerator[3] | 0.8 |
| Antioxidant | 2.50 |

[1]diphenyl guanidine
[2]mercaptobenzothiazole disulfide
[3]N-tert-butyl-2-benzothiazole sulfenamide

TABLE II

| Sample No. | 1 | 2 | 3 | 4 |
| --- | --- | --- | --- | --- |
| Polysulfide Ex 1 | 0 | 2.0 | 0 | 0 |
| Polysulfide Ex 2 | 0 | 0 | 0 | 2.0 |
| Polysulfide Ex 3 | 0 | 0 | 2.0 | 0 |
| Rheometer | | | | |
| $T_1$ (min) | 3.5 | 1.78 | 1.59 | 1.84 |
| $T_{90}$ (min) | 9.02 | 6.07 | 5.22 | 5.97 |
| Tmin | 3.15 | 2.8 | 3.89 | 3.06 |
| Tmax | 15.59 | 14.67 | 14.28 | 13.7 |
| Del T | 12.44 | 11.87 | 10.39 | 10.64 |
| ML 1 + 4 @ 100° C. | 38.0 | 41.0 | 75.5 | 45.5 |
| G' @ 3%, 60° C. (MPa) | 2.29 | 2.35 | 2.23 | 2.10 |
| G' @ 10% | 1.67 | 1.72 | 1.75 | 1.58 |
| Tan Delta @ 3%, 60° C. | 0.202 | 0.205 | 0.149 | 0.187 |
| Tan Delta @ 10%, 60° C. | 0.182 | 0.190 | 0.145 | 0.173 |
| G' @ 0.2% (MPa) | 4.04 | 3.83 | 3.18 | 3.28 |
| G' @ 20% (MPa) | 1.41 | 1.44 | 1.51 | 1.36 |
| G' @ 2%/G' @ 20% | 2.86 | 2.65 | 2.11 | 2.42 |

The above results show that, with the presence of the polysulfides, the Mooney viscosity of the compounds increase indicating an increase in rubber stiffness. The decrease in Tan Delta values at 3 percent and lowered G' ratio indicate improved rubber-to-filler interaction and better filler dispersion.

EXAMPLE 5

Physical Testing

Table III below shows the basic rubber compound that was used in this example. The rubber compound was prepared in a two-stage Banbury mix. All parts and percentages are by weight unless otherwise noted.

All samples were prepared with the same procedure and ingredients except as to the respective amount (phr) of components listed in Table IV. The physical data for each sample is also listed in Table IV.

TABLE III

| Non-Productive | (phr) |
|---|---|
| Emulsion Polymerized SBR[1] | 100.0 |
| Carbon Black (N299) | 50.0 |
| Polysulfide of Example 1, 2 or 3 | Varied |
| Stearic Acid | 2.0 |
| Naphthenic Oil | 5.0 |
| Waxes | 1.5 |
| Zinc Oxide | 3.0 |
| Accelerator[2] | 0.20 |
| Accelerator[3] | 0.35 |
| Productive | (phr) |
| Sulfur | 1.4 |
| Accelerator[2] | 1.5 |
| Antioxidant | 2.5 |

[1]Commercially available from The Goodyear Tire & Rubber Company as Plioflex 1502.
[2]diphenyl guanidine
[3]mercaptobenzothiazole disulfide
[2]N-cyclohexyl benzothiazole-2-sulfenamide

TABLE IV

| Sample No. | 1 | 2 | 3 | 4 |
|---|---|---|---|---|
| Polysulfide Ex 1 | 0 | 2.0 | 0 | 0 |
| Polysulfide Ex 2 | 0 | 0 | 0 | 2.0 |
| Polysulfide Ex 3 | 0 | 0 | 2.0 | 0 |
| ML 1 + 4 @ 100° C. | 36 | 42.5 | 48 | 39 |
| G' @ 3%, 60° C. (MPa) | 1.37 | 1.50 | 1.68 | 1.54 |
| Tan Delta @ 3%, 60° C. | 0.150 | 0.173 | 0.153 | 0.172 |
| G' @ 0.2% (MPa) | 1.88 | 2.19 | 2.45 | 2.30 |
| G' @ 20% (MPa) | 1.01 | 1.05 | 1.20 | 1.08 |
| G' @ 2%/G' @ 20% | 1.85 | 2.10 | 2.04 | 2.13 |

The above results show that, with the presence of the polysulfides, the Mooney viscosity of the compounds increase indicating an increase in rubber stiffness.

What is claimed is:

1. A method for processing rubber comprising mixing with a rubber from 0.1 to 10 phr of an aromatic ketone polysulfide of the formula

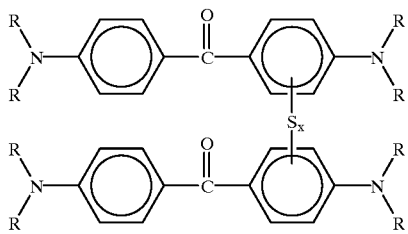

wherein R is selected from the group consisting of alkyls having from 1 to 18 carbon atoms and x is an integer of from 2 to 8.

2. The method of claim 1 wherein R is an alkyl of from 1 to 2 carbon atoms.

3. The method of claim 1 wherein x is an integer of from 2 to 4.

4. The method of claim 1 wherein R is an integer of from 1 to 2 carbon atoms and x is an integer of from 2 to 4.

* * * * *

UNITED STATES PATENT AND TRADEMARK OFFICE
CERTIFICATE OF CORRECTION

PATENT NO.    : 6,277,926 B1
DATED         : August 21, 2001
INVENTOR(S)   : Lawson Gibson Wideman et al.

It is certified that error appears in the above-identified patent and that said Letters Patent is hereby corrected as shown below:

<u>Column 9,</u>
Line 57, change "1500" to -- 150° --

Signed and Sealed this

Twenty-sixth Day of March, 2002

*Attest:*

JAMES E. ROGAN
*Director of the United States Patent and Trademark Office*

*Attesting Officer*